United States Patent [19]

Sparks

[11] Patent Number: 4,663,122
[45] Date of Patent: May 5, 1987

[54] METHOD FOR FLASH STERILIZATION

[76] Inventor: Beverly J. Sparks, 19250 Clement Dr., Castro Valley, Calif. 94552

[21] Appl. No.: 621,037

[22] Filed: Jun. 15, 1984

[51] Int. Cl.⁴ ............................................. A61L 2/06
[52] U.S. Cl. ..................................... 422/26; 422/297; 422/300
[58] Field of Search ................... 422/25, 26, 297, 300, 422/302, 310; 294/27; 206/557, 560, 370; 220/334, 335, 337, 367, 368

[56] References Cited

U.S. PATENT DOCUMENTS

| | | | |
|---|---|---|---|
| 572,815 | 12/1896 | Nicholes | 294/27 |
| 725,123 | 4/1903 | Nichols | 422/300 |
| 2,060,065 | 11/1936 | Gill et al. | 422/297 |
| 2,072,569 | 3/1937 | Shoan | 294/27 |
| 2,289,890 | 7/1942 | Walter | 422/297 |
| 3,458,275 | 7/1969 | Bense et al. | 422/310 |
| 3,942,864 | 3/1976 | Numbers | 220/335 |
| 4,084,080 | 4/1978 | McMahan | 422/26 |
| 4,111,654 | 9/1978 | Fahluik et al. | 422/26 |
| 4,170,421 | 10/1979 | Balding et al. | 422/297 |
| 4,192,845 | 3/1980 | Kalasek | 422/25 |
| 4,195,061 | 3/1980 | Kalasek | 422/25 |
| 4,298,801 | 11/1981 | Heitman et al. | 378/177 |
| 4,342,730 | 8/1982 | Perrotta | 422/26 |
| 4,349,118 | 9/1982 | Sanderson et al. | 422/26 |
| 4,349,508 | 9/1982 | Liede | 422/26 |

FOREIGN PATENT DOCUMENTS

| | | | |
|---|---|---|---|
| 2253694 | 12/1971 | Fed. Rep. of Germany | 422/26 |
| 2,843,052 | 4/1980 | Fed. Rep. of Germany | 422/300 |
| 556345 | 7/1923 | France | 422/297 |

Primary Examiner—David L. Lacey
Attorney, Agent, or Firm—Linval B. Castle

[57] ABSTRACT

The invention is for an instrument container and the method of its use. Instruments for sterilization are placed on a tray spaced above a floor of the container, and the container has a gated exhaust port in a wall and adjacent the floor. In use, the open top container with open exhaust port is placed in a pressure vessel and having an outlet, steam is caused to gravitate down through the instruments to exit through its open exhaust port and thence through the vessel's outlet. When the steam vessel is opened, the gate is closed and latched over the container's exhaust port and a top cover is installed so that the sterilized instruments maybe transported through non-sterile environments without danger of contamination.

3 Claims, 7 Drawing Figures

METHOD FOR FLASH STERILIZATION

BRIEF SUMMARY OF THE INVENTION

This invention relates to high speed or flash sterilization of implements such as surgical instruments and particularly to a novel instrument transport container that permits gravity displacement and complete penetration of superheated pressurized steam upon and through the various instruments on a perforated rack in the container.

Flash sterilization is an effective method for the rapid sterilization of instruments and is accomplished with the use of a gravity displacement, pressurized steam sterilization vessel into which is introduced steam at a gauge pressure of about 27 p.s.i. or more and temperature of about 270° F. or above. The saturated steam is horizontlly introduced into the pressure vessel near the top of one end where it then gravitates down through the vessel and is exhaused through an outlet in a floor of the vessel at the opposite end. The outlet then passes the air/steam mixture through a pressure controlling trap which retains the pure steam.

While flash sterilization is a highly effective system, a problem exists that affects its efficiency. If instruments are placed in a tray or other container within the pressure vessel, the steam will not gravitate into the container but will be blocked by entrapped air in the container and will thus spill over the top and down the sides toward the vessel air outlet. Therefore, to sterilize a tray of instruments in the pressure vessel, a considerable time will be required in order for the air and contents of the instrument tray to reach the ambient high sterilization temperature in the vessel. For effective flash sterilization of instruments, the steam must access every crevice of an instrument and the greatest deterrent to such steam penetration is entrapped air. Therefore, it has heretofore been necessary to place the instruments upon a towel or rack in the pressure vessel so that the gravitating steam may penetrate through the instruments. Then, after the approximate three minutes required for complete flash sterilization, the problem becomes one of removing the very hot instruments from the pressure vessel without recontaminating them with unsterilized removal tools, or of burned fingers through sterilized surgical gloves.

The flash sterilization instrument container of the invention permits rapid and complete sterilization of a relatively large quantity of instruments in a pressurized flash sterilization pressure vessel and, in addition, provides a means for safe removal of the superheated instrument container from the vessel and safe storage of the instruments therein without danger of their recontamination. Therefore, instruments such as surgical instruments may be rapidly and completely sterilized in the container within the pressure vessel and, upon completion of the run, the container with instruments therein may be removed, cooled, carried into a sterile environment and then removed from the container for use.

Briefly described, the flash sterilization instrument container of the invention comprises a comparitively high-walled, metal box that is preferably rectangular. The container has a reasonably tight-fitting top cover and contains a perforated instrument-supporting shelf member that is slightly raised above the container's floor. In one end of the container and as close to the container's floor as possible, is an exhaust port that may be securely closed by a latching gate on the outer wall of the container.

In use, the instrument filled container is placed in the flash sterilization pressure vessel with the top cover removed and the exhaust port gate fully opened. The pressure vessel is sealed and the saturated steam entering the vessel enters the open top of the instrument container, surrounds and flash sterilizes the instruments therein, and exits through the open exhaust port of the instrument container and thence through the outlet of the pressure vessel and air/vapor trap. Thus the steam is not blocked to spill over the top as in a closed-bottom instrument tray container but enters through the top and, in passing toward the exhaust port of the instrument container, engulfs the instruments and results in rapid and complete flash sterilization. Upon completion of the run, the pressure vessel is opened, the top cover which may also have been in the vessel is put on the container, and the exhaust port gate is latched closed. A convenient lifting handle is then used to remove the hot container from the pressure vessel and to transport it as necessary. As long as the exhaust port gate remains closed and the top cover remains on the instrument container, the instruments contained therein remain reasonably safe from being contaminated.

DESCRIPTION OF THE DRAWINGS

In the drawings which illustrate the preferred embodiment of the invention.

DETAILED DESCRIPTION OF THE INVENTION

Figure 1:
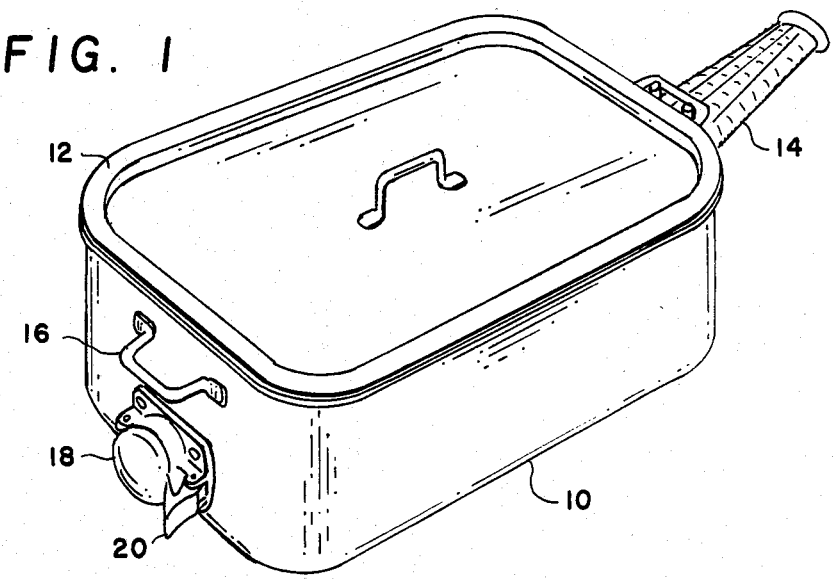
FIG. 1 is a perspective view of the flash sterilization instrument container with exhaust gate closed, top cover installed, and with the lifting handle installed.

FIG. 1 is a perspective view illustrating the flash sterilization instrument container 10 of the invention with a top cover or lid 12 in place and an accessory lifting handle 14 coupled to one of the end handles 16 of the container. The container 10 may be of any convenient size such as approximately eighteen inches in length, ten inches in width, and six inches in height and is preferably constructed of stainless steel. Located in one end of the preferably rectangular container 10 and as close to the bottom thereof as possible is an exhaust port that is illustrated to be closed by a gate 18 that is hinged at one side so that the gate may remain open or closed and locked by a latch 20. The exhaust port through the lower end surface of the container should have a relatively large diameter of, for example, 1½ inches so that it does not restrict the flow of saturated steam from the instrument container. When the cover 12 is installed and the gate 18 closed, as illustrated, instruments that have been previously sterilized in the container 10 may be transported from the flash sterilizing vessel through a non-sterile area to another sterile environment without danger of contamination.

Figure 2:
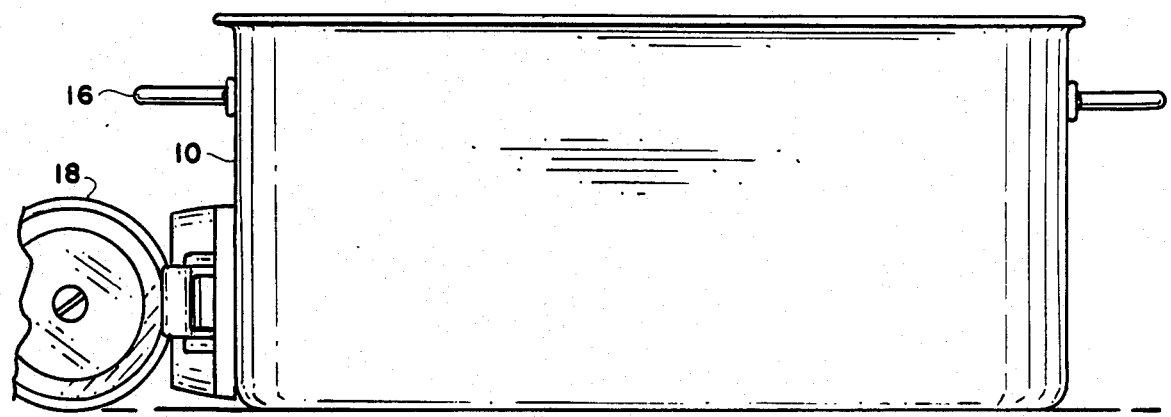
FIG. 2 is a side elevational view of the container with exhaust gate open and top cover removed.

FIG. 2 is a side elevational view illustrating the instrument container 10 shown with the top cover 12 removed and the exhaust port gate 18 open. This figure illustrates the preferred approximate location of the exhaust port and its gate 18 at the lowest convenient position in the end surface of the container.

Figure 3:
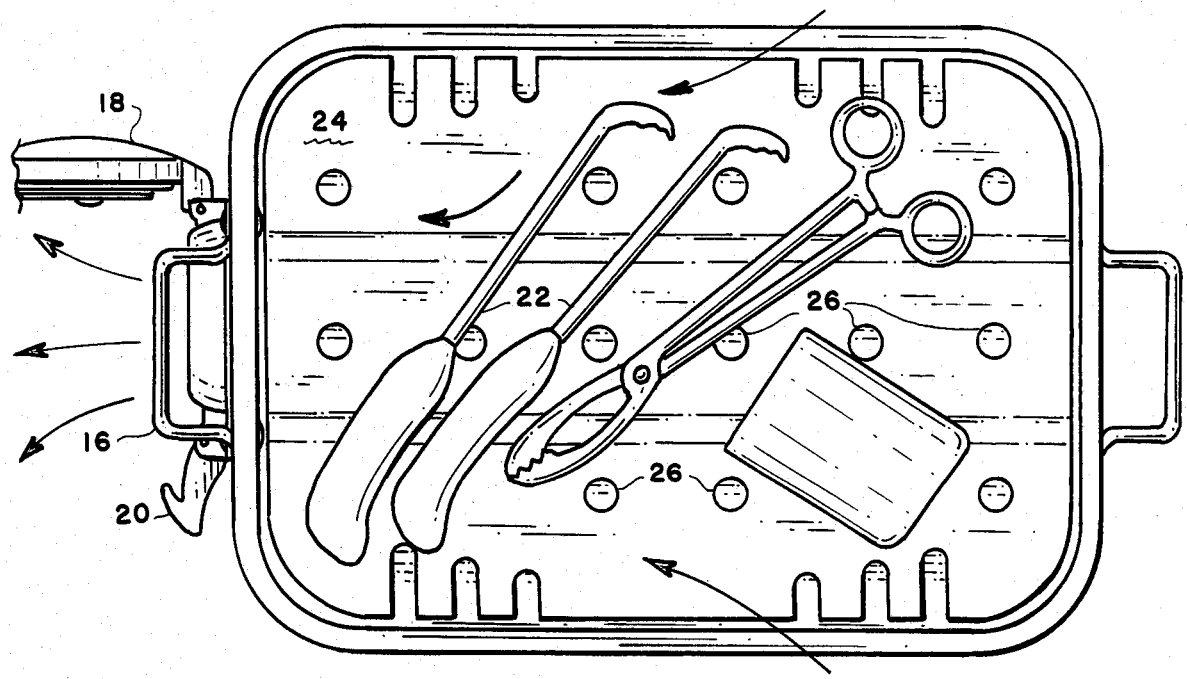
FIG. 3 is a plan view of an instrument container illustrated with various instruments on a perforated raised shelf near the floor of the container.
Figure 4:
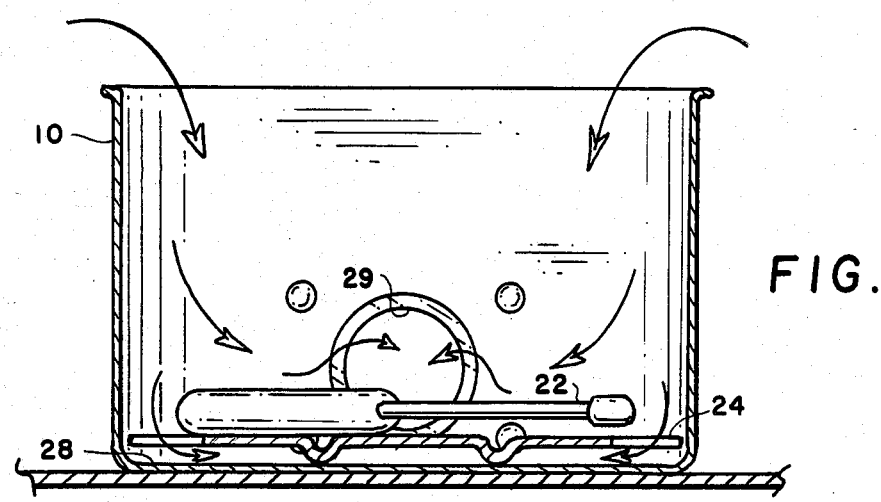
FIG. 4 is a sectional end view of the instrument container illustrating the relative positioning of the raised shelf and exhaust port.

FIG. 3 is a plan view of the opened container of FIG. 2 illustrating the opened exhaust gate 18 and various instruments 22 supported on a thin metal false floor or shelf 24 that is suspended above the floor 28 of the container and which contains a plurality of perforations 26. FIG. 4 is a sectional end elevational view of the container of FIG. 3 and illustrates the preferred approximate spacing between the container floor 28 and the thin metal instrument shelf 24. It will be noted that the exhaust port 29 is at the lowest convenient position in the end of the container so that saturated steam paths, indicated by the arrows, will pass around and penetrate all parts of the instruments before gravitating through the exhaust port 29 and into the pressure vessel.

Figure 5:
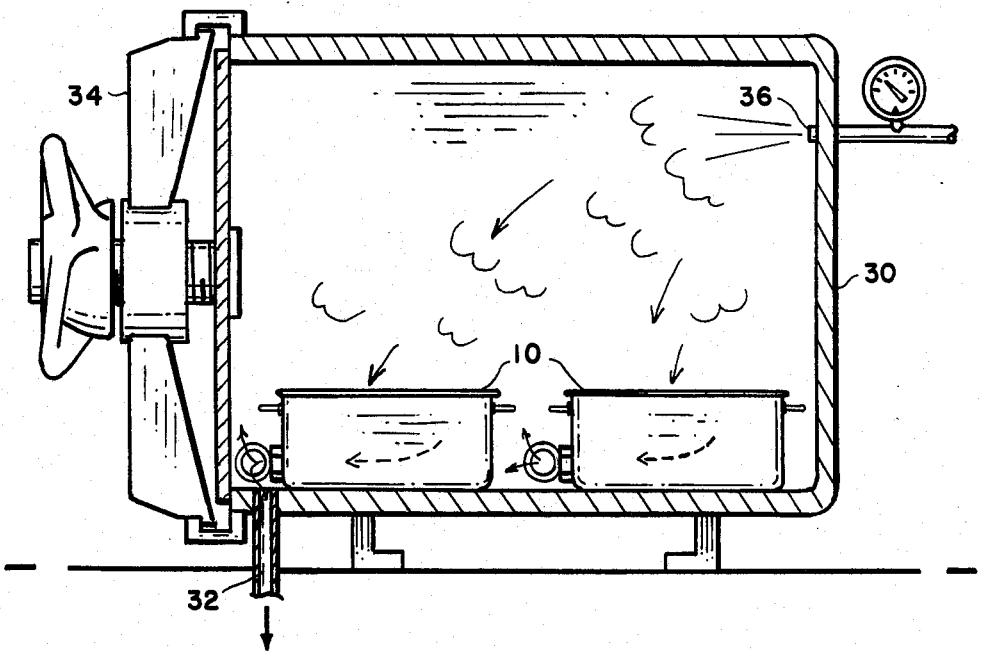
FIG. 5 is a sectional side elevational view of a typical flash sterilization pressure vessel containing two instrument containers with open tops and exhaust port gates.
Figure 6:
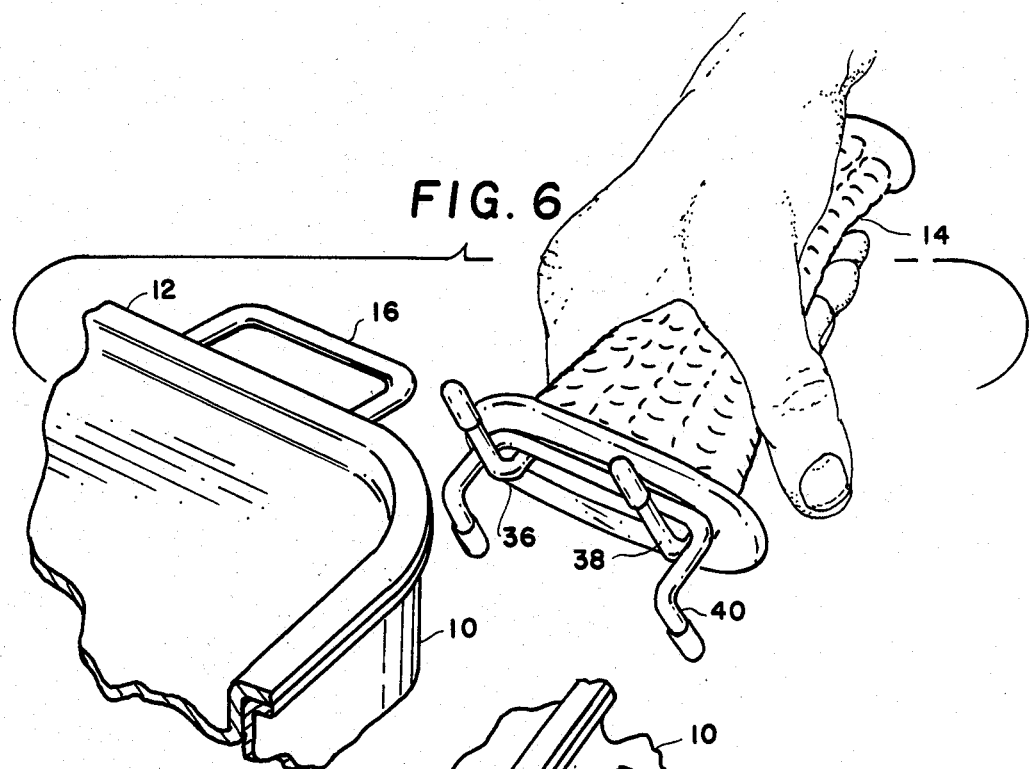
FIG. 6 is a perspective view illustrating the lifting handle for removing the container from the pressure vessel and for transporting it as desired.
Figure 7:
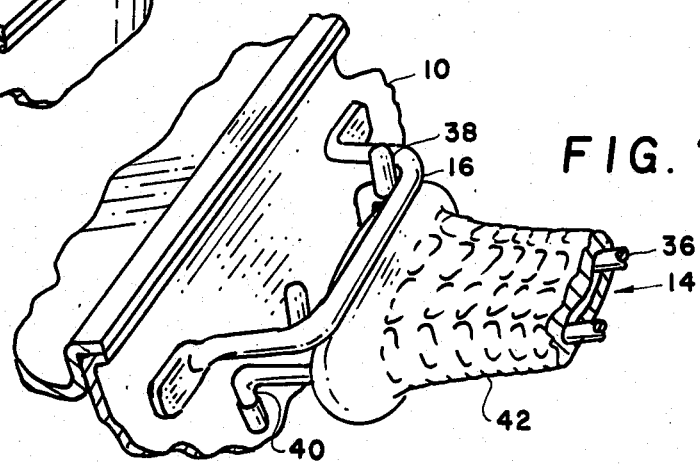
FIG. 7 is another perspective view illustrating the connecting of the lifting handle to the end handle on the instrument container.

FIGS. 5, 6 and 7 illustrate the operation of flash sterilization using the instrument container. One or more containers 10 with instruments placed on the perforated shelves, as shown in FIG. 3 and 4, and with top covers 12 removed and exhaust gates 18 open, are placed on the floor of a gravity displacement steam sterilizer 30 with the exhaust ports of the instrument containers facing the outlet 32 in the floor of the sterilizer or vessel 30, as shown. If desired, two or more containers may be arranged in tandem or in parallel, but it is important that their exhaust ports be generally facing the outlet 32 of the sterilizer vessel 30 so that the steam flowing through the container toward the vessel outlet 32 be minimally restricted.

The door 34 of the pressure vessel 30 is closed and sealed and saturated steam at a temperature of approximately 270° or above is admitted into the vessel 30 through an inlet 36 positioned high on the end opposite the vessel's outlet 32 so that there will be a steam flow that gravitates downward and across the interior of the vessel. Because the instrument containers 10 are in the path of the steam flow, and since there is nothing in the containers such as entrapped air to deflect the steam or cause it to spill over the containers without entering, the steam will enter through the open container tops and will thoroughly penetrate through the contained instruments before passing through the container's open exhaust port and out through the vessel's outlet 32 to an air/steam trap in the flash sterilization system.

After three or more minutes of exposure to the saturated high temperature steam, the contents of the pressure vessel 30 are completely sterilized. The sealed door 34 is opened and the lifting handle 14, shown in FIG. 1 and in greater detail in FIGS. 6 and 7, is preferably used to place the top cover 12 on the container, close and latch the exhaust port gate 18, and remove the now loosely sealed container with sterilized instruments from the flash sterilization vessel to a sterile environment for use of the instruments.

FIGS. 6 and 7 illustrate the preferred embodiment of the lifting handle 14 and its method of use on the container 10. As shown in the figures the handle 14 is formed of a generally U-shaped wire frame 36 having about one inch of each end thereof turned up at substantially right angles to form an upturned hook portion 38 having a width between ends that will enable the upturned hook to fit into the end handles 16 on the instrument container 10. A second wire is formed into a downturned hook 40 and bridges the wires near the upturned hook portion that extends out from the upturned portion 38 by an amount approximately equal to the amount of extension of the end handles 16 from the end surface of the container. Thus, the upturned portions of the handle engage the end handles of the container while the downturned hook bears against the outer surface of the container as shown in FIG. 7. The lifting handle 14 is preferable covered with a suitable cushioned cover 42, such as a bicycle handle-bar grip, that will also provide temporary thermal insulation from the metal portions of the handle.

Having thus described the flash sterilization instrument container and its method of use, what is claimed is:

1. A method for the rapid and thorough flash sterilization of instruments in a gravity displacement steam pressure sterilizing vessel in which steam at a temperature of at least 270° F. is admitted into said vessel through an inlet at a point high in a wall of said vessel and gravitates through said vessel to an outlet at a point low and adjacent a wall of said vessel opposite said inlet wall, said method comprising the steps of:

placing instruments to be sterilized on a perforated shelf positioned in an open topped, high solid walled, box container having a solid flat floor, said shelf being spaced above the solid floor of said container, said container having an open exhaust port of substantially 1½ inches in diameter in a wall and adjacent said floor, and a manually operable latchable gate on the outer surface of said wall for opening and closing said exhaust port;

positioning said container in the gravity displacement steam sterilizing vessel with the open top of said container below the level of the steam admitting point of said sterilizing vessel;

sealing said sterilizing vessel;

admitting steam through said steam admitting inlet of said vessel, the steam thus admitted gravitating through the open top of said box container, said instruments in said container, said container exhaust port, and through said vessel outlet; and continuing the flow of steam through said sterilizing vessel for a period of at least three minutes.

2. The method of claim 1 wherein said step of positioning said container in said sterilizing vessel further includes the step of positioning said container with the open exhaust port thereof directed toward the outlet of said sterilizing vessel.

3. The method claimed in claim 1 further including the steps of: discontinuing the flow of steam through said admitting inlet; opening said sterilizing vessel;

applying a cover to the open top of said instrument container;

closing and latching said gate over the exhaust port of said instrument container; and removing said instrument container from said sterilizating vessel.

* * * * *